US011813044B2

(12) United States Patent
De Groot et al.

(10) Patent No.: US 11,813,044 B2
(45) Date of Patent: Nov. 14, 2023

(54) DEVICE AND METHOD FOR NON-INVASIVE ASSESSMENT OF MAXIMUM ARTERIAL COMPLIANCE

(71) Applicant: KONINKLIJKE PHILIPS N.V., Eindhoven (NL)

(72) Inventors: Koen Theo Johan De Groot, Sevenum (NL); Antonius Hermanus Maria Akkermans, Veldhoven (NL); Cornelus Hendricus Bertus Arnoldus Van Dinther, Mierlo (NL); Stefan Pfundtner, Eindhoven (NL); David Antoine Christian Marie Roovers, Eindhoven (NL); Alphonsus Tarcisius Jozef Maria Schipper, Stramproy (NL); Cornelis Harm Taal, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 1227 days.

(21) Appl. No.: 16/309,950

(22) PCT Filed: Jun. 14, 2017

(86) PCT No.: PCT/EP2017/064632
§ 371 (c)(1),
(2) Date: Dec. 14, 2018

(87) PCT Pub. No.: WO2017/216268
PCT Pub. Date: Dec. 21, 2017

(65) Prior Publication Data
US 2019/0159688 A1 May 30, 2019

(30) Foreign Application Priority Data
Jun. 14, 2016 (EP) .................. EP16174325

(51) Int. Cl.
A61B 5/021 (2006.01)
A61B 5/02 (2006.01)
(Continued)

(52) U.S. Cl.
CPC ...... *A61B 5/02141* (2013.01); *A61B 5/02007* (2013.01); *A61B 5/02225* (2013.01);
(Continued)

(58) Field of Classification Search
CPC ............ A61B 5/02141; A61B 5/02007; A61B 5/02225; A61B 5/6824; A61B 5/0059;
(Continued)

(56) References Cited

U.S. PATENT DOCUMENTS 3,920,004 A 11/1975 Nakayama
5,111,817 A 5/1992 Clark
(Continued)

FOREIGN PATENT DOCUMENTS

EP 0188894 A1 7/1986
EP 0627191 A1 7/1994
(Continued)

OTHER PUBLICATIONS

Tomlinson, L.A. et al., "Methods for Assessing Arterial Stiffness: Technical Considerations", Wolters Kluwer Health, pp. 655-660, vol. 21, No. 6, Nov. 2012.
(Continued)

*Primary Examiner* — Matthew Kremer
*Assistant Examiner* — Kyle W. Kretzer (57) ABSTRACT

The present invention relates to a device (10) for determining an arterial compliance of a subject (12). The device (10) comprises an inflatable cuff (14), a pressure sensor (18) which is configured to sense a pressure signal (52) that is indicative of a pressure within the cuff (14), a second sensor (20) which is at least partly integrated in the cuff (14) and
(Continued)

configured to sense a second signal (56) that is responsive to expansions and contractions of the cuff (14) caused by a pulsating blood flow in an artery (50) of the subject (12), and a processing unit (22). The processing unit is configured to determine based on said part of the pressure signal (52) a pulse pressure of the subject (12), to determine based on said part of the second signal (56) an arterial volume change of the artery (50) of the subject (12) during at least one cardiac cycle, and to determine the arterial compliance of the subject (12) based on pulse pressure and the arterial volume change.

17 Claims, 3 Drawing Sheets

(51) Int. Cl.
  *A61B 5/022* (2006.01)
  *A61B 5/00* (2006.01)
(52) U.S. Cl.
  CPC .......... *A61B 5/6824* (2013.01); *A61B 5/0059* (2013.01); *A61B 5/02108* (2013.01); *A61B 2562/0233* (2013.01)
(58) Field of Classification Search
  CPC ........ A61B 5/02108; A61B 2562/0233; A61B 5/022; A61B 5/02233; A61B 2562/0266
  See application file for complete search history.

(56) References Cited

U.S. PATENT DOCUMENTS

| | | | |
|---|---|---|---|
| 8,840,561 B2 | 9/2014 | Lane | |
| 2003/0095263 A1* | 5/2003 | Varshneya | A61B 5/4818 356/477 |
| 2006/0247538 A1* | 11/2006 | Davis | A61B 5/02125 600/490 |
| 2009/0259131 A1* | 10/2009 | Tsuji | A61B 5/022 600/493 |
| 2010/0094140 A1 | 4/2010 | Pranevicius | |
| 2011/0009718 A1 | 1/2011 | Gavish | |
| 2011/0015531 A1 | 1/2011 | Fujii | |
| 2014/0135634 A1* | 5/2014 | Pranevicius | A61B 5/02225 600/492 |
| 2016/0029901 A1 | 2/2016 | Kuri | |

FOREIGN PATENT DOCUMENTS

| | | | | |
|---|---|---|---|---|
| EP | 0588982 B1 | 3/2001 | | |
| WO | WO-9222239 A1 * | 12/1992 | ......... | A61B 5/02007 |
| WO | WO9222239 A1 | 12/1992 | | |

OTHER PUBLICATIONS

Drzewiecki, G. et al., "Non-Invasive Measurement of the Human Brachial Artery Pressure—Area Relation in Collapse and Hypertension", Annals of Biomedical Engineering Society, vol. 26, pp. 965-974, 1998.

Liu, S-H. L. et al., "A New Oscillometry-Based Method for Estimating Brachial Artery Compliance Under Loaded Conditions", IEEE Transbiomed Eng. 2008.

Dziuda, L. et al., "Fiber-Optic Sensors for Monitoring Patient Physiological Parameters: A Review of Applicable Technologies and Relevance to Use During Magnetic Resonance Imaging Procedure", Journal of Biomedical Optics, vol. 20, No. 1, pp. 010901-1-010901-23, Jan. 2015.

PCT International Search Report, International application No. PCT/EP2017/064632, dated Sep. 13, 2017.

Observations On the PCT International Search Report and the Written Opinion of International Application No. PCT/EP2017/064632, dated Aug. 7, 2018.

* cited by examiner

DEVICE AND METHOD FOR NON-INVASIVE ASSESSMENT OF MAXIMUM ARTERIAL COMPLIANCE

CROSS-REFERENCE TO RELATED APPLICATIONS

This patent application claims the priority benefit under 35 U.S.C. § 371 of international patent application no. PCT/EP2017/064632, filed Jun. 14, 2017, which claims the priority benefit European patent Application No. 16174325.7, filed on Jun. 14, 2016, the contents of which are hereby incorporated by reference herein.

FIELD OF THE INVENTION

The present invention relates to a device for non-invasive blood pressure monitoring and for determining an arterial compliance. The present invention also relates to a corresponding method for determining an arterial compliance of a subject.

BACKGROUND OF THE INVENTION

It is anticipated that in the near future the advent of wearable on-body sensors enables a shift from conventional hospital treatment by replacing it with wearable sensor technologies, centered around the individual, to provide better information about the subject's general health. It is expected that such vital sign monitor systems shall reduce treatment costs by disease prevention and enhance the quality of life and, potentially, improved physiological data for the physician to analyze when attempting to diagnose the subject's general health conditions. Vital signs monitoring typically includes monitoring one or more of the following physical parameters: Heart rate, blood pressure, respiratory rate and core body temperature. A further vital sign, which is considered to become more and more important, is the so-called vessel or arterial stiffness.

The present invention focuses on determining the blood pressure and a parameter to describe the arterial stiffness.

In the US about 30% of the adult population has high blood pressure. Only about 52% of this population have their condition under control. Hypertension is a common health problem which has no obvious symptoms. Blood pressure generally arises with aging and the risk of becoming hypertensive in later life is considerable. About 66% of the people in age group 65-74 do have a high blood pressure. Persistent hypertension is one of the key risk factors for strokes, heart failure and increased mortality. A condition of the subject can be improved by lifestyle changes, healthy dietary choices and medication. Particularly for high risk patients, continuous 24 hour blood pressure monitoring is very important by means of systems which do not impede ordinary daily life activities. Blood pressure is usually measured as two readings: systolic and diastolic pressure. Systolic pressure occurs in the arteries during the maximal contraction of the left ventricle of the heart. Diastolic pressure refers to the pressure in the artery when the heart muscle is resting between beats and refilling with blood. Normal blood pressure is considered to be 120/80 mmHg. A person is considered to be hypertensive when the blood pressure is above 140/90 mmHg.

There are two main classes of methods to monitor blood pressure: (a) invasive direct blood pressure monitoring and (b) non-invasive indirect blood pressure monitoring.

Invasive direct blood pressure monitoring may be done e.g. by catheterization, which is the gold standard to measure blood pressure. A strain gauge in fluid is placed in direct contact with blood at an artery side. This method is only used when an accurate continuous blood pressure monitoring is required in dynamic (clinical) circumstances. It is most commonly used in intensive care medicine and anesthesia to monitor a blood pressure in real time.

Non-invasive indirect blood pressure monitoring may be done e.g. by means of oscillometry. Oscillometry is a way for an automatic, non-invasive measurement of the blood pressure. In oscillometry an inflatable cuff with an integrated pressure sensor is used (see e.g. Alpert et al., Oscillometric Blood Pressure: A review for clinicians, Am. Soc. Hypertension, 2014). The inflatable cuff is placed around an upper arm of a subject approximately at the same height as the heart.

With an electronic oscillometric blood pressure device, air will be pumped into the cuff to a pressure initially above systolic arterial pressure. Hence, the brachial artery is fully occluded obstructing the blood flow through the artery. Next, the pressure in the cuff will be slowly decreased by deflating the cuff to below diastolic pressure. While deflating the cuff, the pressure inside the cuff is measured with an electronic pressure transducer to observe the cuff pressure oscillations. These oscillations occur when blood flow is present, although restricted, as the brachial artery is partly occluded. The oscillations are in synchronicity with the cyclic motion of the artery excited by the pumping heart. The measured pressure waveforms during the deflation period is known as the cuff deflation curve and the measured oscillations in the signal output that superimpose the cuff deflation curve are denoted as oscillometric waveform.

The oscillometric waveform may, for example, be derived from the raw signal of the pressure transducer by means of highpass filtering. One can then determine from the oscillometric waveform the systolic, mean and diastolic pressure by means of appropriate algorithms that are well-known in the field of oscillometry (see e.g. Babbs, Oscillometric Measurement of Systolic and Diastolic Blood Pressures Validated in a Physiologic Mathematical Model, BioMedical Engineering OnLine, 2012 and Raamat et al., Accuracy of Some Algorithms to Determine the Oscillometric Mean Arterial Pressure: A Theoretical Study, Blood Pressure Monitoring, 2013).

The other vital sign which is focused according to the present invention is, as already mentioned above, arterial stiffness. Biological aging and arterial sclerosis drive arterial stiffness. The major causes of arterial stiffness are vascular calcification, progressive degradation of artery elastine fibers and genetic factors. Increased arterial stiffness is associated with an increased risk of cardiovascular events such as myocardial infarction and stroke. Cardiovascular diseases are the number one cause of death globally. An estimated 17.5 million people died from cardiovascular diseases in 2012, representing 31% of all global deaths. Of these deaths, an estimated 7.4 millions were due to coronary heart disease and 6.7 millions were due to stroke. Arterial stiffness is regarded as an independent predictor of cardiovascular morbidity and mortality in hypertensive patients.

Blood pressure has a complex non-linear relationship with arterial wall stiffness. The wall stiffness of an artery is not constant but depends on both the blood pressure and smooth muscle contraction. In the context of arterial stiffness, blood pressure is best represented by the mean arterial pressure. Well-known arterial wall models that characterize arterial elastic mechanics can be found in Tomlinson, Methods for Assessing Arterial Stiffness: Technical Considerations, Wolters Kluwer Health, 2012.

The present invention particularly focuses on a parameter to describe the arterial stiffness. A reliable parameter to describe the arterial stiffness is the so-called arterial compliance which is well-known in the art. Arterial compliance $C_{art}$ is a measure of vascular volume change $\Delta V_{art}$ in response to a change in blood pressure $\Delta P$, i.e. $C_{art} = \Delta V_{art}/\Delta P$.

There are numerous approaches in the prior art for assessing/estimating the arterial compliance in a non-invasive and user-friendly way. A typical approach is known from Drzewiecki et al., Non-Invasive Measurement of the Human Brachial Artery Pressure—Area Relation in Collapse and Hypertension, 1998 as well as from Liu, A New Oscillometry-Based Method for Estimating Brachial Artery Compliance under loaded conditions, IEEE Transbiomed Eng. 2008. These methods use an inflatable cuff to assess the arterial compliance. Since the cuff is elastic and contains compressed air, the cuff itself has its own compliance $C_{cuff}$. The cuff compliance is the non-linear relation between cuff volume $V_{cuff}$ and cuff pressure $P_{cuff}$ and is caused by the effect of Boyle's law and tightness of the cuff applied to the upper arm. When knowing in advance $C_{cuff}$, one can derive the vascular volume change from the observed cuff pressure change by computing $\Delta V_{art} = C_{cuff} \cdot \Delta P_{cuff}$.

A huge disadvantage of the above-mentioned method is that it requires an accurate representation of the cuffs volume-pressure relation $C_{cuff}$, meaning that it is necessary to determine the cuff compliance $C_{cuff}$ at every value of cuff pressure. This relation is not fixed and needs to be recalibrated over time and may therefore introduce systematic errors when assessing arterial compliance.

As proposed by Liu (see reference above), a mathematical model may be used to estimate the cuff compliance $C^I_{cuff}$ during the inflation period from the air cuff volume $V^I_{cuff}$ and pressure inside the cuff $P^I_{cuff}$ that is measured by a pressure transducer. The air cuff volume $V^I_{cuff}$ is estimated by integrating the signal F from an airflow sensor. Arterial volume change $V_{art}$ is predicted from the observed cuff pressure $P^D_{cuff}$ and amplitude oscillations AO during cuff deflation and by incorporating the cuff compliance model $C^I_{cuff}$. The arterial compliance $C_{art}$ in turn is estimated from the estimated $V_{art}$ and the observed pressure changes in the cuff. In this approach $V_{art}$ is indirectly estimated from the cuff pressure changes during the deflation period. This may again yield to systematic errors.

US 2006/0247538 A1 discloses a method of noninvasively obtaining the vessel compliance and/or the vessel segmentation. A series of pressure values are applied to a region of the vessel to adjust the transmural pressure of the vessel wall. At each of the pressure values at least one of a pulse transit time and a pulse wave velocity through the region of the vessel is measured. At least one of vessel compliance and vessel segmentation is determined as a function of the pulse transit time or pulse wave velocity and the applied pressure.

US 2014/0135634 A1 discloses a method to obtain continuous recording of the central arterial blood pressure waveform noninvasively utilizing dual (distal occlusion and proximal) brachial artery occlusion cuffs and dual external osculation. The distal arterial occlusion cuff eliminates venous stasis artifact and flow related gradient from aorta to the brachial artery. The proximal cuff measures, and delivers, dual external oscillation. The dual external oscillation allows measurement of the arterial compliance at a multitude of transmural pressure values during each cardiac cycle. Transmural pressure/arterial compliance and arterial pressure curves are subsequently reconstructed using dual external oscillation. The curves consist of two parts, rapid and slow parts, both at the frequency higher than the arterial pulse.

SUMMARY OF THE INVENTION

It is therefore an object of the present invention to provide a device and method for determining an arterial compliance of a subject which overcome the problems and disadvantages of the above-mentioned methods according to the prior art. It is particularly an object of the present invention to find a way for assessing the arterial compliance in a direct, comparatively more exact, yet user-friendly way.

In a first aspect of the present invention a device for determining an arterial compliance of a subject is presented that comprises:
  an inflatable cuff which is attachable to a body part of the subject;
  inflation and deflation means for inflating and deflating the cuff;
  a pressure sensor which is configured to sense a pressure signal that is indicative of a pressure within the cuff;
  a second sensor which is at least partly integrated in the cuff and configured to sense a second signal that is responsive to expansions and contractions of the cuff caused by a pulsating blood flow in an artery of the subject; and
  a processing unit which is configured:
  (i) to evaluate at least parts of the pressure signal and the second signal that are recorded while the cuff is attached to the body part of the subject and being deflated from above systolic pressure to below diastolic pressure,
  (ii) to determine based on said part of the pressure signal a pulse pressure of the subject,
  (iii) to determine based on said part of the second signal an arterial volume change of the artery of the subject for each of a plurality of cardiac cycles recorded while the cuff is being deflated from above systolic pressure to below diastolic pressure; and
  (iv) to determine the arterial compliance of the subject either by determining a maximum arterial volume change of the arterial volume changes determined for each of the plurality of cardiac cycles and dividing the maximum arterial volume change by the pulse pressure,
  or by dividing each of the determined arterial volume changes of the plurality of cardiac cycles by the pulse pressure to receive a plurality of arterial compliance values, and then determining a maximum of the plurality of arterial compliance values.

In a second aspect of the present invention, a method for determining an arterial compliance of a subject is presented, wherein the method comprises the steps of:
  attaching an inflatable cuff to a body part of the subject;
  inflating the cuff to a first pressure above systolic pressure;
  deflating the cuff to a second pressure below diastolic pressure;
  sensing a pressure signal that is indicative of a pressure within the cuff while the cuff is being deflated from above systolic pressure to below diastolic pressure;
  sensing a second signal that is responsive to expansions and contractions of the cuff caused by a pulsating blood flow of the subject while the cuff is deflated from above systolic pressure to below diastolic pressure;

determining a pulse pressure of the subject, based on the pressure signal;

determining, based on the second signal, an arterial volume change of an artery of the subject for each of a plurality of cardiac cycles recorded while the cuff is being deflated from above systolic pressure to below diastolic pressure; and determining the arterial compliance of the subject based on the pulse pressure and the arterial volume change either by determining a maximum arterial volume change of the arterial volume changes determined for each of the plurality of cardiac cycles and dividing the maximum arterial volume change by the pulse pressure, or by dividing each of the determined arterial volume changes of the plurality of cardiac cycles by the pulse pressure to receive a plurality of arterial compliance values, and then determining a maximum of the plurality of arterial compliance values.

Preferred embodiments of the invention are defined in the dependent claims. It shall be understood that the claimed method has similar and/or identical preferred embodiments as the claimed device and as defined in the dependent claims.

The inventors of the present invention have found a way for directly assessing the arterial compliance of a subject in a non-invasive, user-friendly manner. In contrast to the above-mentioned methods from the prior art (see Drzewieck et al. and Liu) the measurement does not require an indirect calculation for which the compliance of the cuff needs to be determined. The presented device and method are therefore less error-prone and require less time for preparation and calculation.

The direct measurement of the arterial compliance is possible according to the present invention, since the herein presented device uses an extra sensor (denoted as second sensor) that is especially dedicated for sensing a signal (denoted as second signal) that is responsive to expansions and contractions of the cuff caused by the pulsating blood flow in the artery of the subject. These expansions and contractions of the cuff are proportional to the changes of the arterial cross section in the area of the body part to which the cuff is attached. The changes in arterial cross section again are proportional to the absolute arterial volume changes. Due to the second sensor it is thus possible to sense a signal that is—at least roughly estimated—directly proportional to the arterial volume changes. It is thus easily possible to determine/estimate the arterial volume changes based on the second signal, such that the arterial compliance may be directly assessed based on the known relationship $C=\Delta V_{art}/\Delta P$, where $\Delta V_{art}$ is the arterial volume change determined based on the second signal, and $\Delta P$ is the pulse pressure (systolic pressure–diastolic pressure) that may be calculated based on the pressure signal, e.g. by means of an oscillometric evaluation.

A further advantage of the herein presented approach is that both sensors, i.e. the pressure sensor and the second sensor, are at least partly integrated in the cuff (meaning that at least parts of said sensors are integrated in the cuff, while other parts of the sensors may or may not be integrated in the cuff). Both sensors are thus positioned at close proximity of the artery and are thus capable of precisely determining/estimating the parameters used for the calculation of the arterial compliance of the subject (i.e. the pulse pressure and the arterial volume change). The calculations are thereby independent of the compliance of the cuff.

The processing unit is configured:

to determine the arterial volume change based on the second signal for a plurality of cardiac cycles while the cuff is being deflated from above systolic pressure to below diastolic pressure, to determine a maximum arterial volume change for one of the plurality of cardiac cycles; and to determine the arterial compliance of the subject based on the pulse pressure and the maximum arterial volume change.

In other words, the subject's arterial compliance is associated to the maximum arterial compliance that is estimated during the cuff deflation period. It is clear that instead of determining a maximum arterial volume change, it is also possible to determine the arterial compliance in the abovementioned way for each of the recorded cardiac cycles and then afterwards determine the maximum arterial compliance based on the values calculated for the arterial compliance for each cardiac cycle. Both methods are considered to be equivalent.

According to an embodiment, the processing unit is configured to determine the pulse pressure of the subject based on the pressure signal by means of an oscillometric evaluation. The processing unit may thus derive the oscillometric pressure waveform signal from the pressure signal in the known way by e.g. highpass filtering. The processing unit may then determine the mean arterial pressure, since the mean arterial pressure is equal to the mean cuff pressure at the time instant where the maximum oscillations occur in the oscillometric pressure waveform signal. The processing unit may then calculate the systolic pressure $P_s$ and the diastolic pressure $P_d$ based on the mean arterial pressure by means of well-known algorithms. One of such algorithms is known, for example, from Raamat et al., Accuracy of Some Algorithms to Determine the Oscillometric Mean Arterial Pressure: A Theoretical Study, Blood Pressure Monitoring, 2013. The pulse pressure $\Delta P$ may then be determined by computing $\Delta P = P_s - P_d$.

According to a further embodiment, the processing unit may be configured to determine the pulse pressure of the subject not only based on the pressure signal, but also based on the second signal.

The second signal also includes the amplitude oscillations that are caused by the pulsating blood flow in the artery of the subject. The oscillometric waveform that is a prerequisite of the oscillometric evaluation may thus be also derived from the second signal, such that the amplitude oscillations could be derived from the second signal, while the cuff deflation curve is still derived from the pressure signal. The determination of the systolic and diastolic blood pressure would be still based on the same oscillometric principle. However, it would be also possible to evaluate the oscillometric waveform based on both the pressure signal and the second signal. This would lead to a more robust evaluation of the pulse pressure.

According to a further embodiment of the present invention, the second sensor includes an optical sensor.

The optical sensor preferably uses a microbending optical fiber. In particular, the optical sensor preferably comprises an optical fiber which is integrated into the cuff, a light source which is configured to produce light that is coupled into the optical fiber at a first end of the optical fiber, and a light detector which is configured to detect the light at a second end of the optical fiber opposite the first end. The light detector is preferably configured to transform the detected light into an electrical signal that is proportional to an intensity of the detected light and that represents the second signal. An example of such a fiber-optic sensor that is, however, used for a different purpose is exemplarily known from Dziuda, Fiber-Optic Sensors for Monitoring Patient Physiological Parameters: A Review of Applicable Technologies and Relevance to Use During Magnetic Resonance Imaging Procedure, Journal of Biomedical Optics, 2015.

In practice, any perturbation of the optical fiber integrated in the cuff produces a change in the optical signal which is indicative for the excitation of the fiber. Since the cuff is expanded and contracted in an oscillatory manner due to the pulsating blood flow in the artery of the subject, physical repetitive/oscillatory movement induced by the partly and non-occluded artery will cause a corresponding oscillatory signal part within the optical signal (second signal). This oscillatory signal part may be easily extracted by means of an appropriate signal processing/signal filtering. A change in the optical output signal detected by means of the light detector relative to the optical input signal generated by the light source is thus directly proportional to the arterial volume change in response to a change in transmural arterial blood pressure induced by the arm cuff when deflating the cuff. In other words, the pulsating blood flow causes a repetitive shape change of the optical fiber. This shape change of the optical fiber will change the light intensity that is detected at the light detector, since depending on the shape of the optical fiber more or less light generated by the light source will reach the light detector. Hence, the change of light intensity is directly proportional to the perturbation of the fiber.

According to an embodiment, the cuff comprises an inflatable part and a stretchable carrier material connected to the inflatable part, wherein the optical fiber is integrated in the stretchable carrier material. This has the advantage that the shape changes of the optical fiber will be as large as possible and as continuous as possible.

According to a further embodiment, it is preferred that the stretchable carrier material is arranged at a side of the cuff that is configured to contact the skin of the subject. This ensures that the influence of the inflation and deflation of the inflatable part of the cuff is as low as possible onto the second signal arranging the stretchable material including the optical fiber as close as possible to the subject's skin, furthermore increases the preciseness of the measurement.

According to a further preferred embodiment, the optical fiber is arranged in the cuff as a folded winding. The optical fiber is preferably not fully wound around the circumference of the cuff as a direct loop, but rather arranged as folded winding embedded in the stretchable carrier material. It is especially preferred that the optical fiber comprises at least two folded windings, since this maximizes the sensing area and accuracy of the second sensor. Another option to improve the sensitivity is to use two stretchable carrier material layers, wherein the optical fiber is positioned between the two layers.

As an alternative to the usage of an optical sensor, the second sensor may include a strain gauge. This strain gauge would work according to a similar measurement principle as the optical sensor described above. The expansions and contractions of the cuff caused by the pulsating blood flow in the subject's artery lead to an oscillating electrical signal generated by the strain gauge. This signal may represent the second signal discussed above.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
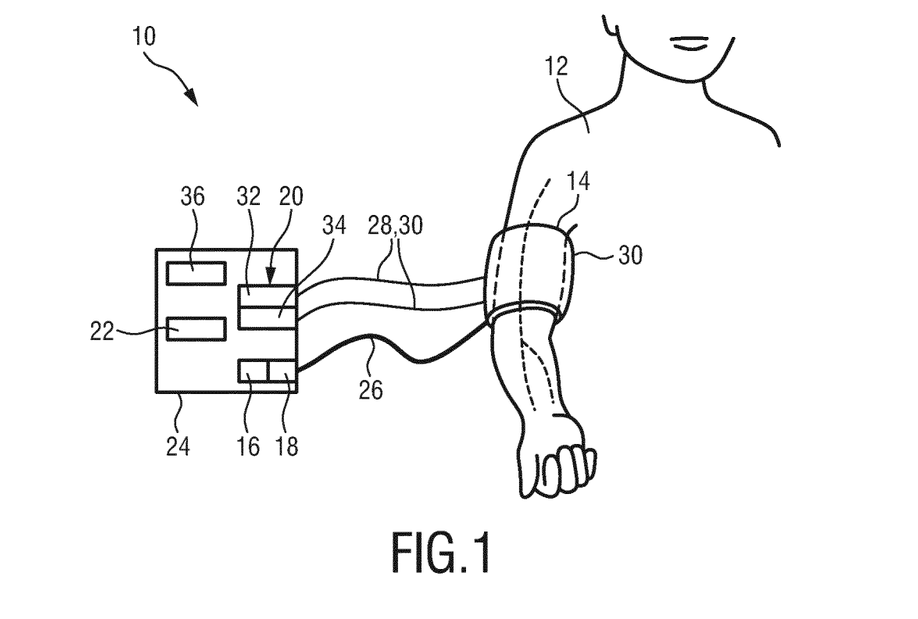
FIG. 1 shows a first embodiment of a device according to the present invention.

FIG. 1 shows an exemplary embodiment of a device for determining an arterial compliance of a subject. The device is therein denoted in its entirety with reference numeral 10. The subject, i.e. a human, is denoted in FIG. 1 with reference numeral 12.

The device 10 comprises an inflatable cuff 14, means 16 for inflating and deflating the inflatable cuff 14, a pressure sensor 18, a second sensor 20, and a processing unit 22. The inflation and deflation means 16, the pressure sensor 18, the second sensor 20 and the processing unit 22 are according to the exemplary example illustrated in FIG. 1 installed in an external housing 24 that is arranged locally remote from the inflatable cuff 14. The inflatable cuff 14 is in the example shown in FIG. 1 attached to an upper arm of the subject 12. The inflatable cuff 14 is connected to the pressure sensor 18 via a hose 26. This hose 26 is also connected to the inflation/deflation means 16. The inflatable cuff 14 is furthermore connected to the second sensor 20 via one or more data connections 28.

It shall be noted that only parts of the second sensor 20 are according to the example given in FIG. 1 installed in the external housing 24, while at least one part 30 is integrated into the inflatable cuff 14. According to the embodiment illustrated in FIG. 1, this part 30 of the second sensor 20 includes an optical fiber, as will be discussed in detail further below. The optical fiber 30 is preferably also used as data connection 28 between the part of the optical fiber 30 that is integrated into the inflatable cuff 14 and a light source 32 and a light detector 34 which are in this example installed in the external housing 24.

It shall be noted that FIG. 1 illustrates an embodiment of the device 10 according to the present invention wherein the fewest possible parts of the device 10 are integrated into the inflatable cuff 14, namely only parts of the second sensor 20 (i.e. the optical fiber 30). However, also the other parts of device 10, i.e. the inflation/deflation means 16, the pressure sensor 18, the processing unit 22, the light source 32 and/or the light detector 34, may generally each be integrated into the inflatable cuff 14 as well, either partly or as a whole. For example, all of these components could be integrated into the inflatable cuff 14. In another example, all components except the processing unit 22 may be integrated into the inflatable cuff 14, while the processing unit 22 is arranged remote from the inflatable cuff 14 and connected to the pressure sensor 18 and the second sensor 20 by means of a wireless data connection. In yet another example of the device 10, the components 16-22 may be distributed such that they are arranged in a plurality of different external housings.

The device 10 according to the present invention may optionally further comprise a display 36. This display 36 may also be either arranged remote from the inflatable cuff 14 (e.g. installed in the external housing 24) or it may be integrated into the inflatable cuff 14.

Figure 3:
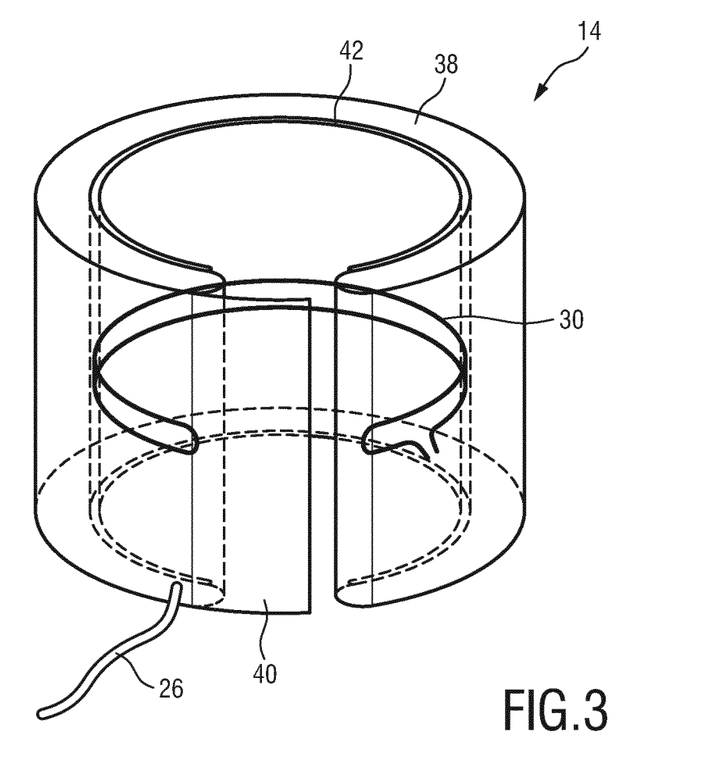
FIG. 3 shows an exemplary embodiment of an inflatable cuff that may be used as part of the device according to the present invention.

FIG. 3 shows an exemplary example of the inflatable cuff 14 in an enlarged, transparent view. According to the therein illustrated example, the inflatable cuff 14 comprises an inflatable part 38. This inflatable part 38 is connected via the hose 26 to the inflating/deflating means 16. The inflating/deflating means 16 may comprise a pump for inflating the inflatable part 38, and a valve for deflating the inflatable part 38. The inflatable part 38 preferably comprises one or more sealed chambers which may be filled up with air.

Figure 4:
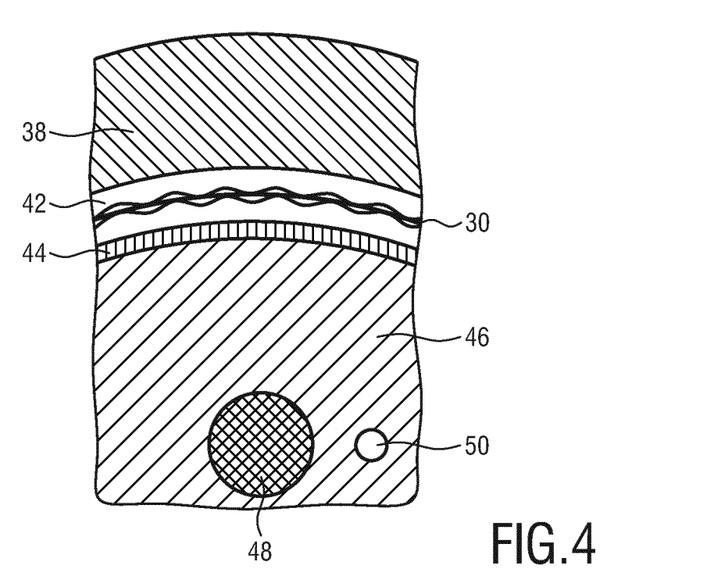
FIG. 4 shows a schematic view of a cross section of the cuff shown in FIG. 3 while being positioned at an upper arm.

The inflatable cuff 14 furthermore comprises a fixation means 40 that may e.g. comprise a hook- and -loop fastener (Velcro® fastener). The inflatable cuff 14 may be therefore easily attached to a suitable body part of the subject 12, e.g. onto an upper arm. According to the embodiment shown in FIG. 3, the inflatable cuff 14 further comprises the optical fiber 30. As it is shown in FIG. 3, the optical fiber 30 is preferably not fully wound around the inflatable cuff 14 as a direct loop, but arranged as a folded winding. The optical fiber 30 is preferably integrated into a stretchable carrier material 42. This stretchable carrier material 42 preferably covers one side of the inflatable part 38 that contacts the skin of the subject 12 when the inflatable cuff 14 is attached to the upper arm of the subject 12. The same may be seen in the cross section illustrated in FIG. 4, where reference numeral 44 indicates the skin of the subject 12, reference numeral 46 indicates the muscle of the subject 12, reference numeral 48 indicates a bone of the subject 12 and reference numeral 50 indicates an artery of the subject 12.

Figure 2:
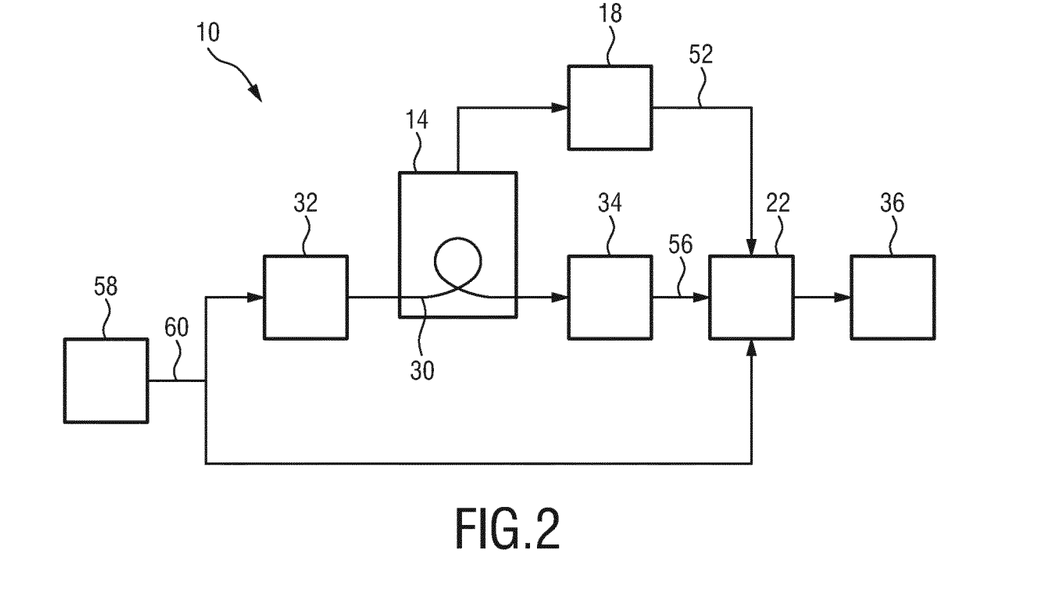
FIG. 2 shows a block diagram illustrating a control model for controlling the device according to the embodiment shown in FIG. 1.

The mode of operation of the device 10 may be explained best with reference to the schematic control model illustrated in FIG. 2. The pressure sensor 18 senses a pressure signal 52 that is indicative of a pressure within the inflatable cuff 14, i.e. within the inflatable part 38 of the inflatable cuff 14. This pressure signal 52 is transmitted to the processing unit 22. An example of such a signal is schematically illustrated in FIG. 5.

Figure 5:
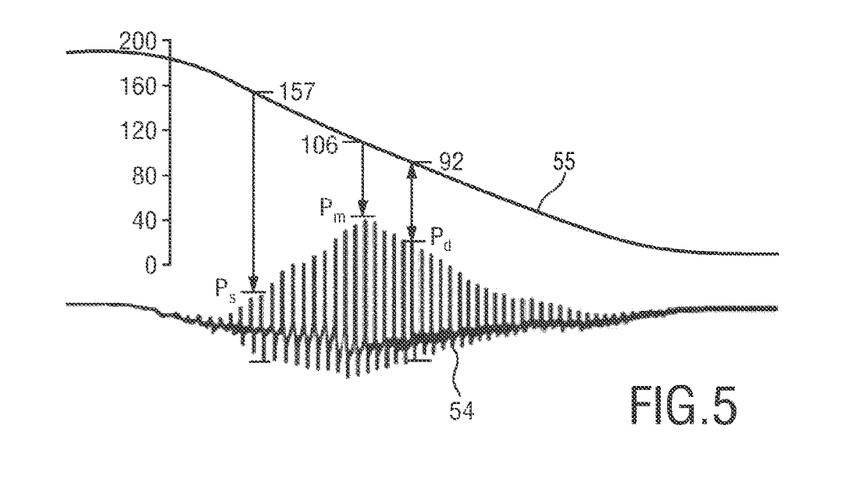
FIG. 5 illustrates an exemplary pressure signal monitored by means of a pressure sensor that may be part of the device according to the present invention.

FIG. 5 shows the pressure within the inflatable cuff 14 over time. The pressure signal 52 is also denoted as inflatable cuff deflation curve. It may be seen that the inflatable cuff 14 is initially inflated to a pressure that is above systolic pressure. Hence, the brachial artery 50 is fully occluded obstructing the blood flow through the artery. The pressure within the inflatable cuff 14 is then slowly decreased by deflating the inflatable cuff 14 to below diastolic pressure. While deflating the inflatable cuff 14, the pressure inside the inflatable cuff 14 is measured with the pressure sensor 18 leading to the pressure signal 52.

The pressure signal 52 is not only influenced by the actively reduced pressure within the inflatable part 38 of the inflatable cuff 14, but also contains signal parts that are due to the pulsating blood flow within the brachial artery 50 of the subject 12. These signal parts are oscillating signal parts that occur shortly before the pressure within the inflatable cuff 14 is reduced to the systolic pressure and remain in the pressure signal 52 even after the pressure is reduced below diastolic pressure, i.e. almost until the pressure within the inflatable cuff 14 is completely reduced to atmospheric pressure.

The oscillating signal parts of the pressure signal 52 that are induced by the pulsating blood flow may be filtered out from the pressure signal 52. The oscillometric waveform 54 that results from said filtering step is shown in the lower part of FIG. 5.

The processing unit 22 is configured to analyze the pressure signal 52, to derive the oscillometric waveform 54 therefrom, and to then determine the blood pressure of the subject 12 based on an inflatable cuff deflation curve 55 and the oscillometric waveform 54. This may be done by means of an oscillometric evaluation. By means of appropriate oscillometric algorithms one can determine from the oscillometric waveform 54 the systolic pressure, the mean pressure and the diastolic pressure. Usually, the mean pressure is determined first, since the mean arterial pressure is approximately equal to the mean cuff pressure at the point where the maximum oscillations occur within the oscillometric waveform 54. The mean arterial pressure is therefore comparatively easy to determine (106 mmHg in the example shown in FIG. 5). The systolic pressure and the diastolic pressure (systolic pressure and diastolic pressure are in the example given in FIG. 5 at 157 mmHg and 92 mmHg) may be determined by the processing unit 22 based on the mean arterial pressure that has been determined beforehand. Algorithms for such an oscillometric evaluation are well-known in the art.

Simultaneously to receiving the pressure signal 52, the processing unit 22 also receives a second signal 56 from the second sensor 20. The second signal 56 is generated as follows: A signal source 58 generates a control signal 60 that is input to the light source 32 and the processing unit 22. Based on this control signal 60 the light source 32 produces light that is coupled into the optical fiber 30 at a first end of the optical fiber 30. The light is then guided through the optical fiber 30, as the light is kept in the core by total internal reflection. However, the pulsating blood flow in the brachial artery 50 of the subject 12 causes a modulation of the light within the optical fiber 30. This may be detected by the light detector 34 as variations in the light intensity of the light received at the light detector 34. The light detector 34 detects the light at a second end of the optical fiber 30 opposite the first end to which the light source 32 is coupled. The change of the light intensity detected at the light detector 34 is directly proportional to the perturbation of the optical fiber 30. The second signal 56 generated by the light detector 34 is thus responsive to expansions and contractions of the inflatable cuff 14 caused by the pulsating blood flow in the brachial artery 50 of the subject 12. The second signal 56 may of course also include signal parts that relate from shape changes within the inflatable cuff 14 that result from the deflation of the inflatable part 38. However, since the optical fiber 30 is integrated into the stretchable carrier material 42 that is positioned on the inside of the inflatable part 38 close to or in contact with the skin 44 of the subject 12 (see FIG. 4) those signal parts are insignificant or may be at least filtered out. The remaining signal parts of the second signal 56 are indicative of the movements of the inflatable cuff 14 caused by the pulsating blood flow. These signal parts are thus proportional to the changes of the cross section of the brachial artery 50 over time, and therefore also proportional to the arterial volume change.

Thus, the arterial volume oscillations during heartbeats may be monitored with the aid of the observed optical transmission loss and amplitude oscillations of the light which reflect the change in arterial volume.

In order to extract the arterial amplitude oscillations from the second signal 56, the processing unit 22 may be configured to correlate the control signal 60 and the second signal 56. Based on this, an arterial volume change of the brachial artery 50 of the subject 12 may be calculated or at least estimated by the processing unit 22.

The processing unit 22 may be furthermore configured to finally determine/estimate the arterial compliance of the subject. The arterial compliance of the subject is preferably calculated based on the pulse pressure $\Delta P$ being the difference between the systolic pressure $P_s$ and the diastolic pressure $P_d$, and based on the arterial volume change $\Delta V_{art}$ as follows: $C_{art} = \Delta V_{art}/\Delta P$. The processing unit 22 may either store the calculated arterial compliance $C_{art}$ in a memory for later analysis or it may display the calculated value on the display 36. The processing unit 22 may also be configured to transmit the calculated data via an antenna to an external computing, display and/or storage device.

The arterial compliance $C_{art}$ is preferably calculated within the processing unit 22 as follows: The processing unit 22 derives from the pressure signal 52 the oscillometric waveform 54 and estimates the systolic pressure $P_s$ and diastolic pressure $P_d$ based on oscillometric waveform 54. The processing unit 22 then calculates the pulse pressure $\Delta P$ by computing $\Delta P = P_s - P_d$. Next, the arterial volume amplitude $V^i_{art}$ is determined for each $i^{th}$ cardiac cycle during the cuff deflation period. For all N-cardiac cycles during the cuff deflation a slope $s^i$ is computed according to $s^i = V^i_{art}/\Delta P$, giving a set $S = \{s^i, \ldots, s^n\}$. The local slope s could be expressed in units of mm²/mmHg. It shall be noted that $V_{art}$ and $\Delta V_{art}$ may be indicated in units of mm² representing a cross-sectional area of the brachial artery 50 that is proportional to the arterial volume. Finally, the processing unit 22 may calculate the arterial compliance $C_{art}$ as $C_{art} = \max(\{s^i, \ldots, s^n\})$. In other words, the subject's arterial compliance $C_{art}$ is associated to the maximum arterial compliance that is estimated during the cuff deflation period.

Figure 6:
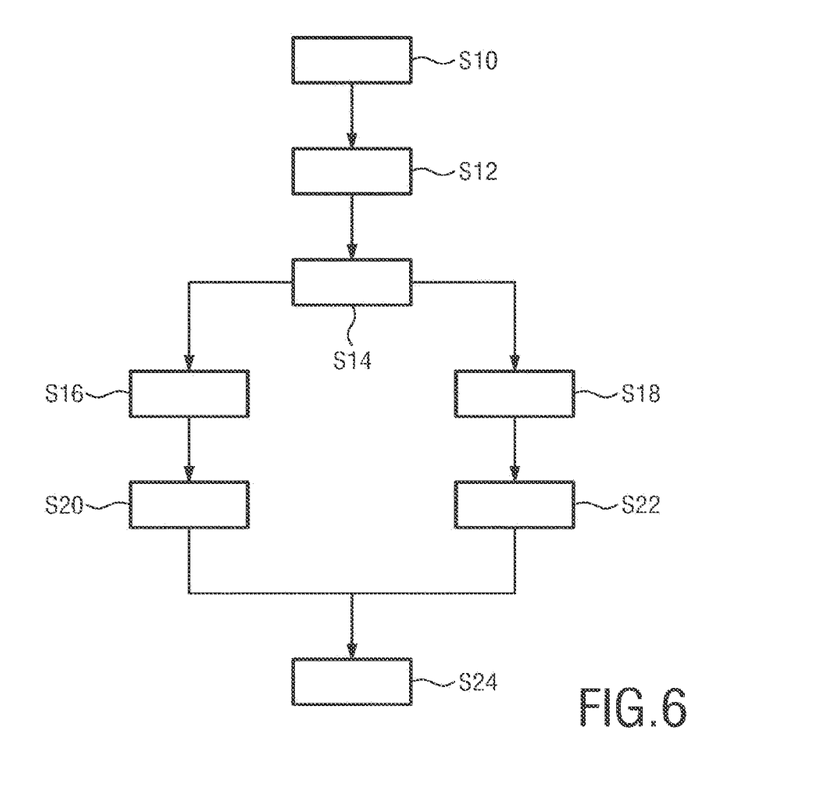
FIG. 6 shows a schematic block diagram illustrating the method according to the present invention.

FIG. 6 summarizes the method according to the present invention in a schematic block diagram. In a first step S10, the inflatable cuff 14 is attached to a body part of the subject 12. The inflatable cuff 14 is then inflated in step S12 to a first pressure that is above systolic pressure $P_s$. Next, the inflatable cuff 14 is deflated in step S14 to a second pressure below diastolic pressure $P_d$. During the deflation of the inflatable cuff 14, the pressure within the inflatable cuff 14 is measured (step S16). Simultaneously in step S18, the second signal is sensed by the second sensor 20. The processing unit 22 then calculates the pulse pressure of the subject based on the pressure signal 52 (step S20). The processing unit 22 also determines an arterial volume change of the brachial artery 50 of the subject during at least one cardiac cycle based on the second signal 56 provided by the second sensor 20 (step S22). Finally, the arterial compliance of the subject 12 is determined in step S24 based on the determined pulse pressure and the arterial volume change.

It shall be noted that the above-illustrated embodiment of the device 10 may also be modified in that a strain gauge is integrated into the inflatable cuff 14 and used instead of the optical fiber 30. Such an electro-chemical sensor would also sense a signal that is responsive to the expansions and contractions of the inflatable cuff 14 caused by the pulsating blood flow in the brachial artery 50 of the subject 12. Such a signal could thus also be used to determine the arterial volume change of the subject.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for determining an arterial compliance of a subject, comprising:
   an inflatable cuff which is attachable to a body part of the subject;
   a pump adapted to inflate and a valve adapted to deflate the inflatable cuff;
   a pressure sensor which is configured to sense a pressure signal that is indicative of a pressure within the inflatable cuff;
   an optical sensor, which is at least partly integrated in the inflatable cuff, and is configured to sense a second signal that is responsive to expansions and contractions of the inflatable cuff caused by a pulsating blood flow in an artery of the subject; and
   a processing unit which is configured:
   to evaluate at least parts of the pressure signal and the second signal that are recorded while the inflatable cuff is attached to the body part of the subject and being deflated from above systolic pressure to below diastolic pressure over a plurality of cardiac cycles,
   to determine based on said part of the pressure signal a pulse pressure ($\Delta P$) of the subject,
   to determine based on said part of the second signal an arterial volume change ($\Delta V_{art}$) of the artery of the subject for each cardiac cycle of the plurality of cardiac cycles recorded while the inflatable cuff is being deflated from above systolic pressure to below diastolic pressure; and
   to determine the arterial compliance (C) of the subject either by determining a maximum arterial volume change ($\Delta V_{art\ max}$) of the arterial volume changes ($\Delta V_{art}$) determined for each cardiac cycle of the plurality of cardiac cycles and dividing the maximum arterial volume change ($\Delta V_{art\ max}$) by the pulse pressure ($\Delta P$),
   or by dividing each of the determined arterial volume changes ($\Delta V_{art}$) of the plurality of cardiac cycles by the pulse pressure ($\Delta P$) to receive a plurality of arterial compliance values, and then determining a maximum of the plurality of arterial compliance values.

2. The device according to claim 1, wherein the processing unit is configured to determine the pulse pressure of the subject based on the pressure signal by an oscillometric evaluation.

3. The device according to claim 2, wherein the processing unit is configured to determine the pulse pressure of the subject not only based on the pressure signal, but also based on the second signal.

4. The device according to claim 1, wherein the optical sensor further comprises an optical fiber.

5. The device according to claim 4, wherein the optical fiber is integrated into the inflatable cuff, the optical sensor further comprising a light source, which is configured to produce light that is coupled into the optical fiber at a first end of the optical fiber, and a light detector, which is configured to detect the light at a second end of the optical fiber opposite the first end.

6. The device according to claim 5, wherein the light detector is configured to transform the detected light into an electrical signal that is proportional to an intensity of the detected light and that represents the second signal.

7. The device according to claim 5, wherein the inflatable cuff comprises an inflatable part and a stretchable carrier material connected to the inflatable part, wherein the optical fiber is integrated in the stretchable carrier material.

8. The device according to claim 7, wherein the stretchable carrier material is arranged at a side of the inflatable cuff that is configured to contact the skin of the subject.

9. The device according to claim 5, wherein the optical fiber is arranged in the inflatable cuff as a folded winding.

10. The device according to claim 9, wherein the optical fiber comprises at least two folded windings.

11. The device according to claim 1, wherein the optical sensor further comprises a strain gauge.

12. A method for determining an arterial compliance of a subject, the method comprising:
attaching an inflatable cuff to a body part of the subject;
inflating the inflatable cuff to a first pressure above systolic pressure;
deflating the inflatable cuff to a second pressure below diastolic pressure;
receiving a pressure signal from a pressure sensor that is indicative of a pressure within the inflatable cuff while the inflatable cuff is being deflated from above systolic pressure to below diastolic pressure;
receiving a second signal from an optical sensor that is responsive to expansions and contractions of the inflatable cuff caused by a pulsating blood flow of the subject while the inflatable cuff is deflated from above systolic pressure to below diastolic pressure over a plurality of cardiac cycles;
determining a pulse pressure ($\Delta P$) of the subject based on the pressure signal;
determining, based on the second signal, an arterial volume change ($\Delta V_{art}$) of an artery of the subject for each cardiac cycle of the plurality of cardiac cycles recorded while the inflatable cuff is being deflated from above systolic pressure to below diastolic pressure; and
determining the arterial compliance of the subject as a maximum arterial compliance value associated with one cardiac cycle of the plurality of cardiac cycles, wherein the maximum arterial compliance value is determined by:
determining a maximum arterial volume change ($\Delta V_{art\ max}$) of the arterial volume changes ($\Delta V_{art}$) determined for each cardiac cycle of the plurality of cardiac cycles and dividing the maximum arterial volume change ($\Delta V_{art\ max}$) by the pulse pressure ($\Delta P$) to obtain the maximum arterial compliance value, or
dividing each of the determined arterial volume changes ($\Delta V_{art}$) of the plurality of cardiac cycles by the pulse pressure ($\Delta P$) to receive a plurality of arterial compliance values, and then determining a maximum of the plurality of arterial compliance values to obtain the maximum arterial compliance value.

13. The method according to claim 12, wherein the pulse pressure of the subject is determined by an oscillometric evaluation either based on the pressure signal or based on the pressure signal and the second signal.

14. A method implemented by a processing unit for determining an arterial compliance of a subject, the method comprising:
receiving a pressure signal from a pressure sensor that is indicative of a pressure within an inflatable cuff attached to a body part of the subject while the inflatable cuff is being deflated from above systolic pressure to below diastolic pressure over a plurality of cardiac cycles;
receiving a second signal from an optical sensor that is responsive to expansions and contractions of the inflatable cuff caused by a pulsating blood flow of the subject while the inflatable cuff is deflated from above systolic pressure to below diastolic pressure over the plurality of cardiac cycles;
determining a pulse pressure ($\Delta P$) of the subject, based on the pressure signal;
determining, based on the second signal, an arterial volume change ($\Delta V_{art}$) of an artery of the subject for each cardiac cycle of the plurality of cardiac cycles recorded while the inflatable cuff is being deflated from above systolic pressure to below diastolic pressure; and
determining the arterial compliance of the subject as a maximum arterial compliance value associated with one cardiac cycle of the plurality of cardiac cycles, wherein the maximum arterial compliance value is determined by:
determining a maximum arterial volume change ($\Delta V_{art\ max}$) of the arterial volume changes ($\Delta V_{art}$) determined for each cardiac cycle of the plurality of cardiac cycles and dividing the maximum arterial volume change ($\Delta V_{art\ max}$) by the pulse pressure ($\Delta P$) to obtain the maximum arterial compliance value, or
dividing each of the determined arterial volume changes ($\Delta V_{art}$) of the plurality of cardiac cycles by the pulse pressure ($\Delta P$) to receive a plurality of arterial compliance values, and then determining a maximum of the plurality of arterial compliance values to obtain the maximum arterial compliance value.

15. A device for determining an arterial compliance of a subject, comprising a processing unit that is configured:
to receive a pressure signal from a pressure sensor indicative of pressure in an inflatable cuff attached to a body part of the subject and a second signal from an optical senor indicative of intensity of light in an optical fiber in the inflatable cuff;
to evaluate at least parts of the pressure signal and the second signal that are recorded while the inflatable cuff is being deflated from above systolic pressure to below diastolic pressure over a plurality of cardiac cycles;
to determine based on said part of the pressure signal a pulse pressure ($\Delta P$) of the subject;
to determine based on said part of the second signal an arterial volume change ($\Delta V_{art}$) of an artery of the subject for each cardiac cycle of the plurality of cardiac cycles recorded while the inflatable cuff is being deflated from above systolic pressure to below diastolic pressure; and to determine the arterial compliance (C) of the subject as a maximum arterial compliance value associated with one cardiac cycle of the plurality of cardiac cycles, wherein the maximum arterial compliance value is determined by:

determining a maximum arterial volume change ($\Delta V_{art\ max}$) of the arterial volume changes ($\Delta V_{art}$) determined for each cardiac cycle of the plurality of cardiac cycles and dividing the maximum arterial volume change ($\Delta V_{art\ max}$) by the pulse pressure ($\Delta P$) to obtain the maximum arterial compliance value, or dividing each of the determined arterial volume changes ($\Delta V_{art}$) of the plurality of cardiac cycles by the pulse pressure ($\Delta P$) to receive a plurality of arterial compliance values, and then determining a maximum of the plurality of arterial compliance values to obtain the maximum arterial compliance value.

16. The device according to claim 15, wherein the processing unit is further configured to determine the pulse pressure of the subject based on the pressure signal by an oscillometric evaluation.

17. The device according to claim 16, wherein the processing unit is configured to determine the pulse pressure of the subject further based on the second signal.

\* \* \* \* \*